July 24, 1973 W. W. KNICELY ET AL Plant Pat. 3,370
AZALEA PLANT
Filed March 26, 1971
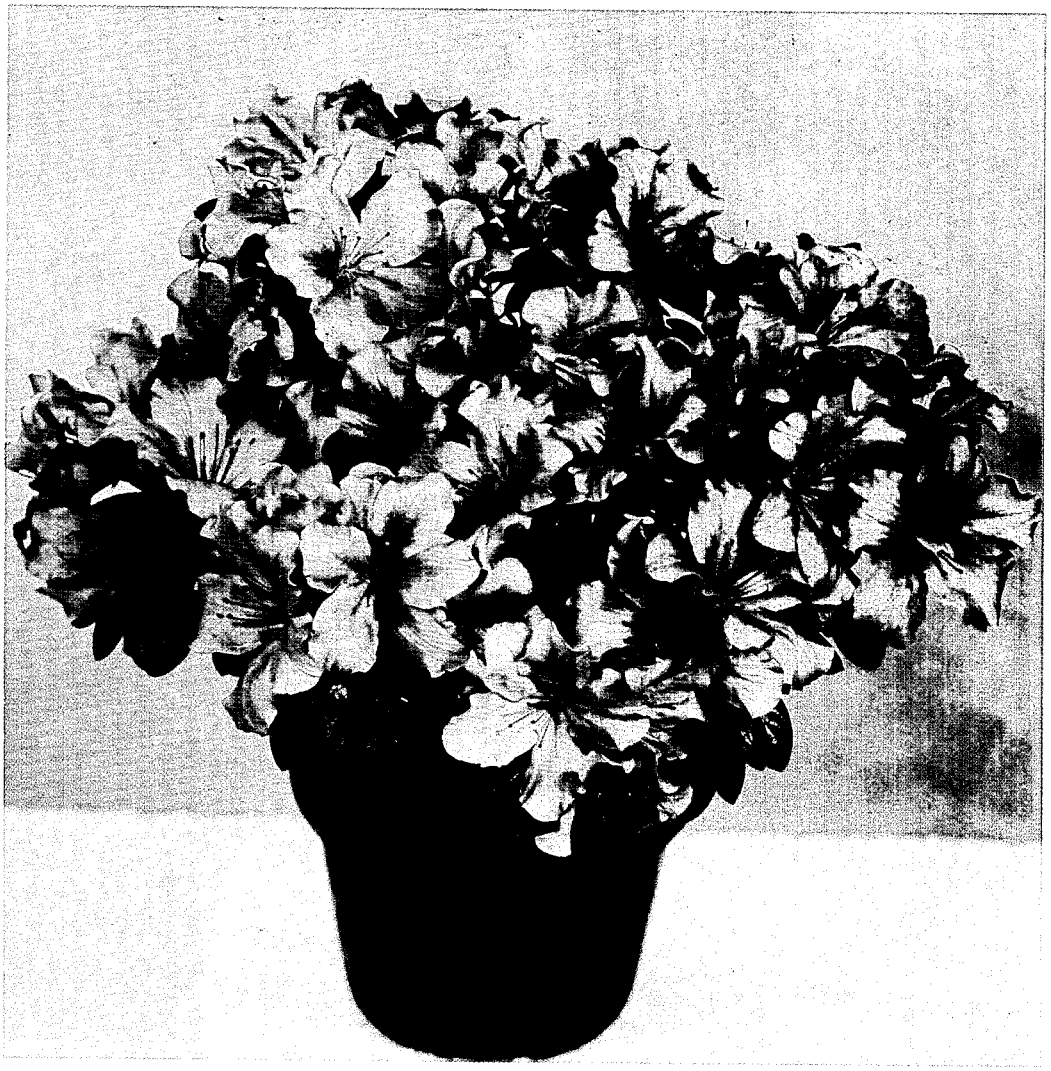
INVENTORS
WALTER W. KNICELY,
WILLIAM E. DUFFETT
BY
Oberlin, Maky, Donnelly & Renner
ATTORNEYS

United States Patent Office

Plant Pat. 3,370

Patented July 24, 1973

3,370
AZALEA PLANT

Walter W. Knicely, Barberton, and William E. Duffett, Akron, Ohio, assignors to Yoder Brothers, Inc., Barberton, Ohio

Filed Mar. 26, 1971, Ser. No. 128,594

Int. Cl. A01h *5/00*

U.S. Cl. Plt.—57 1 Claim

The present invention comprises a new and distinct cultivar of azalea plant resulting from crossing certain azalea selections in a program of controlled hybridization. The seed parent is identified by #36 and the pollen parent by #1040. Both of these parents are unnamed and unpatented and identified by the above numbers to distinguish the parents from other parents in the breeding program.

The new cultivar is similar in many respects to the cultivar Dorothy Gish, having the same characteristics as Dorothy Gish of an early season response and ease of budding and forcing. The new cultivar is distinguished from Dorothy Gish by the following characteristics when grown under comparable conditions:

1. Color a more intense orange rather than salmon.
2. Flower form is a single, semi-double; not a hose-on-hose single.
3. Flowers approximately one-half to one inch larger in diameter.
4. Foliage larger and more glossy green in color.
5. No tendency toward wild water shoot growth.

The new cultivar is also similar in certain respects to the unpatented cultivar Fireglow, which is a sport of the commercially well-known cultivar, Redwing. The cultivar Fireglow referred to herein is not to be confused with the Kurume type evergreen azalea clone arising as a seedling of Hinodegiri, originated by Mayo Nurseries, Augusta, Ga., and referred to on page 264 of Lee, F. D., 1965. The Azalea Book, D. Van Nostrand Co., Inc. The cultivar referred to in the publication is not currently available commercially. The new cultivar has the same characteristics as Fireglow of:

1. An early season response in year-round programs.

2. Ease of budding and forcing.
3. Approximately the same amount of growth from equivalent sized liner.

The new cultivar is distinguished from Fireglow by the following characteristics when grown under comparable conditions:

1. A larger, more glossy foliage.
2. Flowers approximately one-half to one inch larger in diameter.
3. A deeper, more vivid orange color.

The new cultivar was selected from a progeny of seedlings from the above mentioned parents. Varietal worth was determined by flowering liners from cuttings taken from the initial selection in both a year-round and natural season developmental flowering program over a period of four years. Stock growth was evaluated in the vicinity of southern Florida.

The new cultivar has been asexually reproduced by cuttings at Barberton, Ohio, and has been found to retain its distinctive characteristics through successive propagations.

The new cultivar when grown in the vicinity of Barberton, Ohio has a response described as early season, and the following detailed description is based on observations made of the new cultivar in a greenhouse in Barberton, Ohio. The response time and blooming period may vary significantly with varying environmental conditions such as temperature and day length. Suggested flowering period is from December through March in a natural season program, and all 12 months in a year-round controlled program.

The accompanying drawing shows the unique features of the new cultivar, the colors being as nearly true as possible with color illustrations of this type.

The following is a detailed description of the new cultivar. Color references are to the Munsell Color Book, 1963 edition, and comparisons are made to the cultivar Dorothy Gish and Fireglow. Where a value or description appears only for the new cultivar, such value applies also to the comparison cultivars.

Botanical classification: *Rhododendron hybrida* evergreen type

| | Firecrown | Dorothy Gish | Fireglow |
|---|---|---|---|
| Flower: | | | |
| Color (winter color in Barberton, Ohio): | | | |
| General tonality | Orange red, near 7.5R4/10 | Salmon, nearest 2.5R6/12 | Orange red, near 5R/14, not as intense. |
| Sepals first divide | Orange red, near 7.5R4/12 | Salmon pink, near 2.5R5/10 | Orange red, near 5R4/12. |
| Petals unfurl | Orange red, near 7.5R4/10 | Salmon, 3.75R5/12 | Orange red, near 5R5/12. |
| Fully open: | | | |
| Inside of petals | do | Salmon, 2.56/12 | Orange red, near 5R5/14, not as intense. |
| Reverse side of petals | Orange red, lighter than 7.5R4/10 | Salmon, 2.5R6/12, but lighter | Lighter orange red, 5R5/12. |
| Base of petals | Salmon, 5R6/12 | Blush pink, 2.5R9/2 | Salmon pink, 10RP7/8. |
| Outer hose | None | Salmon, nearest 2.5R6/12 | Light pink, nearest 8.75RP6/12, but much lighter, with green. |
| Variations: | | | |
| Blotch | Dark red, 7.5R3/12 | Dark red, near 5R3/10 but darker. | Deep orange red, better 5R4/12 and 5R3/10. |
| Discoloration as ages | Holds relative color as it ages, becomes a dark orange, 5R4/10 when collapsed. | Fades to light salmon, near 2.5R7/6 or lighter before collapsing. | Fades to salmon, 3.75R5/12 or lighter. |
| Bud: | | | |
| Size | Medium | | |
| Form | Conoidal | | |
| Opening habit | Fully expanded petals, rosebud-like, full cup-like; retains cup-like form. | Fully expanded rosebud-like full, open cup-like, retains cup-like form. | Fully expanded rosebud-like full open cup-like retains cup-like form. |
| Bloom: | | | |
| Size | Large | Medium | Medium. |
| Average | 2.8″ | 2″ | 2″. |
| Range | 2″ to 3½″ | 1¾″ to 2⅛″ | 1¾″ to 2⅛″. |
| Borne | Several together | | |
| Average | 2.9 | 3.1 | 2½ |
| Range | 1–4 | 1–4 | 1–5. |
| Form | Slightly semi-double with varying degrees of petaloid anthers. Never fully petaloid. Normal flower calyx. | Hose-on-hose single with completely petaloid calyx. | Single with half formed petaloid hose. |
| Blooming habit | Once, profusely | | |
| Response: | | | |
| Natural season | Early, December flowering possible in all areas of the United States. | | |
| Year-round | Early, sets bud early and uniformly under wide range of environmental conditions. | | |

Botanical classification: *Rhododendron hybrida* evergreen type

| | Firecrown | Dorothy Gish | Fireglow |
|---|---|---|---|
| Sepals "bud sheath" | Normal, smooth hairy, dries up and falls off. | Normal, smooth, somewhat hairy, dries up and falls off. | Normal, smooth, hairy, persistent. |
| Calyx | Normal | Petaloid | Imperfect. |
| Peduncle: | | | |
| Length | Long | Medium | Long. |
| Aspect | Hairy | | |
| Strength | Strong | | |
| Petals: | | | |
| Texture | Soft | | |
| Appearance: | | | |
| Inside | Waxy | Satiny | Satiny. |
| Outside | do | do | Do. |
| Form | Rounded with wavy margins | Rounded with wavy margins | Rounded and somewhat notched. |
| Arrangement | Imbricate | Imbricate | Imbricate. |
| Fragrance | None | | |
| Persistence | Shatter with age | Nonshattering | Shatters readily. |
| Longevity: | | | |
| Greenhouse | 2 weeks | 2 weeks | 7–10 days. |
| Home | 3 weeks | 3 weeks | 2 weeks. |
| Reproductive organs: | | | |
| Stamen | 5–10, some petaloid quite variable | 5–10 some petaloid, quite variable. | 5–10, normal. |
| Another | Normal, deep purple, near 5R2/8 | Normal if present, brownish salmon, near 7.5R6/6. | Normal, purplish red, near 2.5R2/8. |
| Filaments | Thin pubescent, color salmon, near 5R5/10. | Quite thin, smooth, blush pink, 5RP8/6. | Thin, smooth, salmon red, near 3.75R5/14. |
| Style | Generally columnar, color red, near 5R4/14. | Columnar, normal, color salmon pink, near 1.25R6/12. | Columnar, normal, color, base, light salmon pink, 2.5R8/6 blending to dark salmon pink, 1.25R5/12 tip. |
| Stigma | Normal, color brown, near 5YR4/4 | Normal, brownish pink nearest to 5R5/8 but lighter. | Normal, brownish red, near 5R4/10. |
| Ovaries | Hypogynous | | |
| Fruit | None | | |
| Foliage: | | | |
| Type | Evergreen | | |
| Leaflets | Single | | |
| Size: | | | |
| Length average | 2″ | 1⅞″ | 2″. |
| Range | 1″–2¼″ | 1″–2¼″ | ⅞″–2¼″. |
| Width average | 0.8″ | ½″ | ¾″. |
| Range | 0.5–1¼″ | ⅜–⅞″ | ⅜″–1″. |
| Shape | Obovate | | |
| Texture: | | | |
| Upper side | Glossy, waxy | Glossy, waxy | Dull, waxy. |
| Reverse side | Smooth, dull | Glossy | Dull. |
| Rib and mid veins | Slightly depressed | Slightly deressed | Slightly depressed. |
| Edge | Smooth | Smooth | Slightly notched. |
| Color: | | | |
| New foliage: | | | |
| Upper side | Light green 5GY6/8 | Green, 5GY4/6 | Green, 5GY4/6. |
| Reverse side | Light green, 5GY7/8 | Light green, 5GY6/6 | Light green, 5GY6/6. |
| Mature foliage: | | | |
| Upper side | Very dark green, 5GY2/2 | Dark green, 5GY3/4 | Dark green, 10GY2/4. |
| Reverse side | Gray green, 7.5GY4/4 | Gray green, 5GY5/4 | Gray green, 7.5GY4/4. |
| Petiole | Short, hairy light green 5GY7/16 | Short, hairy green, 5GY6/8 | Short, hairy green, 5GY4/6. |
| Plant: | | | |
| Growth habit | Compact, upright with dome top | Compact, semi-upright spreading. | Compact, horizontal. |
| Breaking habit | Vigorous with no wild growth tendencies. | Vigorous with wild growth tendencies. | Vigorous with wild growth tendencies. |
| Size of an average finished product from a #7 liner produced by Yoder Brothers, Inc.: | | | |
| Height | 8″–11″ | 8″–12″ | 6″–9″. |
| Diameter | 10″–15″ | 12″–16″ | 10″–15″. |
| Budding ease | Quite easy under wide range of conditions. | Quite easy under wide range of conditions. | Quite easy under wide range of conditions. |
| Uniformity of budding | Excellent | | |
| Stems, color: | | | |
| New wood | Green, 5GY5/6 | Green, 5GY6/6 | Green, 5GY6/8. |
| Mature wood | Brown, near 10YR4/6 | Brown, 7.5YR3/6 | Brown, 10YR3/4. |
| Cooler tolerance | Good | Very good | Good. |
| Shipping tolerance | do | do | Poor. |
| Recommended flowering period: | | | |
| Year-round | All 12 months | All 12 months | All 12 months. |
| Natural season | Early December thru April | Mid-January thru April | Early January thru April. |

We claim:

1. A new and distinct variety of azalea characterized particularly as to novelty when compared to the cultivar Dorothy Gish by its more intense orange color, its single and semi-double flower form, its not hose-in-hose single, approximately one-half to one inch larger diameter flowers, larger and more glossy green foliage, and its tendency not to have wild water shoot growth; and characterized particularly as to novelty when compared with the cultivar Fireglow by its deeper more vivid orange color, approximately one-half to one inch larger diameter flowers, and its larger, more glossy foliage.

No references cited.

ROBERT E. BAGWILL, Primary Examiner

UNITED STATES PATENT OFFICE
CERTIFICATE OF CORRECTION

PLANT
Patent No. 3,370 Dated July 24, 1973

Inventor(s) WALTER W. KNICELY and WILLIAM E. DUFFETT

It is certified that error appears in the above-identified patent and that said Letters Patent are hereby corrected as shown below:

Below Columns 1 and 2, in tabulation under "Bloom:", opposite "Range", first occurrence, under "Dorothy Gish", "1-3/4" to 2-1/5" " should be --1-3/4" to 2-1/2".

Below Columns 3 and 4, in tabulation under "Reproductive organs:", "Another" should be --Anther--.

Signed and sealed this 1st day of October 1974.

(SEAL)
Attest:

McCOY M. GIBSON JR.
Attesting Officer

C. MARSHALL DANN
Commissioner of Patents